(12) United States Patent
Capecchi et al.

(10) Patent No.: US 7,597,897 B2
(45) Date of Patent: Oct. 6, 2009

(54) MEDICINAL COMPOSITIONS AND METHOD FOR THE PREPARATION THEREOF

(75) Inventors: John T. Capecchi, Oakdale, MN (US); James S. Stefely, Woodbury, MN (US); Peter M. Seiler, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/596,836

(22) PCT Filed: Dec. 10, 2004

(86) PCT No.: PCT/US2004/041194

§ 371 (c)(1), (2), (4) Date: Jun. 27, 2006

(87) PCT Pub. No.: WO2005/066238

PCT Pub. Date: Jul. 21, 2005

(65) Prior Publication Data

US 2008/0267885 A1 Oct. 30, 2008

Related U.S. Application Data

(60) Provisional application No. 60/533,172, filed on Dec. 30, 2003.

(51) Int. Cl.
  *C08G 63/91* (2006.01)
  *A61K 47/34* (2006.01)
  *A61K 9/00* (2006.01)
  C08G 63/00 (2006.01)
  A61K 47/48 (2006.01)
  A61K 9/08 (2006.01)
  A61K 9/16 (2006.01)

(52) U.S. Cl. .................. 424/400; 424/489; 514/772.1; 523/200

(58) Field of Classification Search .................. None
See application file for complete search history.

(56) References Cited

U.S. PATENT DOCUMENTS 5,041,529 A    8/1991  Shinoda et al.

(Continued)

FOREIGN PATENT DOCUMENTS

JP        9059218        3/1997

(Continued)

OTHER PUBLICATIONS

H. Fukazaki et al., "Synthesis of Copoly (D,L-Lactic Acid) with Relatively Low Molecular Weight and In Vitro Degradation," *Eur. Polym. J.*, 25, 1019-1026 (1989).

(Continued)

*Primary Examiner*—Johann R Richter
*Assistant Examiner*—Christopher R Lea

(57) ABSTRACT

Methods for the manufacture of medicinal compositions are described. A method for the manufacture of a medicinal composition according to the invention comprises: (a) Providing a biocompatible polymer of the general formula —[O—$R^1$—C(O)]$_n$— wherein: "$R^1$" is a linear, branched, or cyclic organic group, "n" is at least three, (b) Acylating the biocompatible polymer to provide an acylated biocompatible polymer and a mixed anhydride; (c) Reacting the mixed anhydride with a nucleophile to provide an acylated biocompatible polymer with a terminal carboxylic acid derivative capable of being chemically converted to an acid in the absence of water, (d) Converting the terminal carboxylic acid derivative to an acylated biocompatible polymer with a terminal carboxylic acid; and (e) Combining the acylated biocompatible polymer with a drug to provide the medicinal composition.

35 Claims, 1 Drawing Sheet

U.S. PATENT DOCUMENTS

| | | | |
|---|---|---|---|
| 5,302,693 | A | 4/1994 | Stricker et al. |
| 5,569,450 | A | 10/1996 | Duan et al. |
| 5,618,911 | A | 4/1997 | Kimura et al. |
| 5,714,618 | A | 2/1998 | Kimura et al. |
| 5,871,771 | A | 2/1999 | Zierenberg et al. |
| 6,111,033 | A | 8/2000 | Loughman et al. |
| 6,126,919 | A | 10/2000 | Stefely et al. |
| 6,264,970 | B1 | 7/2001 | Hata et al. |
| 6,416,742 | B1 | 7/2002 | Stefely et al. |
| 2002/0164290 | A1 | 11/2002 | Stefely et al. |
| 2002/0173496 | A1 | 11/2002 | Biggadike |
| 2004/0247561 | A1 | 12/2004 | Seo et al. |
| 2004/0253195 | A1 | 12/2004 | Seo et al. |

FOREIGN PATENT DOCUMENTS

| | | |
|---|---|---|
| JP | 9124778 | 5/1997 |
| WO | WO 94/21229 | 9/1994 |
| WO | WO 03/033592 | 4/2003 |
| WO | WO 03/033593 | 4/2003 |

OTHER PUBLICATIONS

A. Carrio et al., "Preparation and degradation of surfactant-free PLAGA microsphere," *J. Controlled Release*, 37, 113-121 (1995).

P.P. DeLuca et al., "Biodegradable Polyesters for Drug and Polypeptide Delivery," *Polymeric Delivery Systems*; ACS; Chapter 4, 53-77 (1993).

B. Wichert et al., "Low molecular weight PLA: a suitable polymer for pulmonary administered microparticles?". *J. Microencapsulation*, 10, 195-207 (1993).

J.W. Tom et al., Precipitation of Poly(L-lactic acid) and Composite Poly(L-lactic acid)-Pyrene Particles by Rapid Expansion of Supercritical Solutions; *J. Supercritical Fluids*, 7, 9-29 (1994).

R. Wada et al., "New.biodegradable oligoesters for pharmaceutical application," *J. Biomater Sci., Polym. Ed.*, 7, 715-725 (1996).

M. Dittrich, "Purification of biodegradable polymers and oligomers of aliphatic hydroxyl acids", Abstract of Czech Patent No. CZ 278181 (Sep. 15, 1993) Abstract only: CA122(16):188468y.

D. Duan et al., "Oligomeric Lactic Acids as Solubilizing Aids for HFA-Based Metered Dose Inhalers," Biomaterials Technology Center, 3M Corporation, 3M Pharmaceuticals, (Nov. 1998).

D. Duan et al., "Novel Dispersing Aids for Hydrofluoroalkane-Based Metered Dose Inhalers," Biomaterials Technology Center, 3M Corporation, 3M Pharmaceuticals (Nov. 1998).

C. Leach et al., "Metabolism, Distribution, and Toxicity of Oligomeric Lactic Acids Used in Pulmonary Drug Delivery," Biomaterials Technology Center, 3M Corporation, 3M Pharmaceuticals, (Nov. 1998).

J. Stefely et al., "Design and Utility of a Novel Class of Biocompatible Excipients for HFA-Based MDIs," Respiratory Drug Delivery VII, Palm Harbor at Tarpon Springs, FL, 5/14-18, 2000.

MEDICINAL COMPOSITIONS AND METHOD FOR THE PREPARATION THEREOF

This application is a United States national stage filing under 35 U.S.C. § 371 of International Application PCT/US04/41194, filed Dec. 10, 2004, which claims benefit to U.S. Provisional Application 60/533,172, filed Dec. 30, 2003, the disclosure of which is incorporated herein by reference.

This invention relates to methods for the manufacture of medicinal compositions.

BACKGROUND OF THE INVENTION

The delivery of medicinal formulations (e.g., a drug suspended or dissolved in a carrier) to the lungs by way of inhalation is an important means for treating a variety of conditions, including such common conditions as bronchial asthma and chronic obstructive pulmonary disease. Steroids, β-2 agonists, and anti-cholinergic agents are among the drugs that are administered to the lung for such purposes. Such drugs are commonly administered in an aerosol form. To assure that the particles are of a respirable size (e.g., from about 5 to 10 microns in diameter), the particles can first be prepared in an appropriate size and subsequently incorporated into a suspension suitable for use with a propellant to thereby provide an aerosol formulation. Alternatively, formulations can be prepared in solution form in order to avoid the concern for proper particle size in the formulation. Solution formulations must nevertheless be dispensed in a manner that produces particles or droplets of respirable size. Once prepared, aerosol formulations are contained within an appropriate aerosol canister equipped with a metered dose valve. In the hands of a patient, the formulation may then be dispensed via a metered dose inhaler ("MDI") by activating an actuator that directs a predetermined dosage of medication from the valve to the patient.

Aerosol formulations are desirably dispensed from their containers or canisters in a reproducible predetermined dosage. The reproducibility of the dosage can be problematic due to any of a variety of events that may occur in suspension formulations including, for example, rapid creaming, settling, or flocculation. Mechanical problems may also occur to create problems relating to dosage reproducibility. Typical mechanical problems involve valve failure, which can range from the total inoperability of the valve to the partial or sporadic operability accompanying the attempted use of a "sticky" valve. In order to overcome the problems associated with aerosol formulations, such formulations often include surfactants to aid in stabilizing a suspension and thereby facilitate more reproducible dosing. Additionally, some surfactants can also function as lubricants to control and potentially eliminate mechanical problems by providing a measure of lubrication to aid in the smooth actuation of a metered dose valve. Any of a variety of materials may be used as dispersing aids in aerosol formulations. But, the desirability of any particular material is often dependent on the identity of the particular drug and propellant (or class of propellants) being used in a particular medicinal formulation.

One of the recognized difficulties in the formulation of medicinal suspensions and the like has been the difficulty in dissolving sufficient quantities of surfactants in various hydrofluoroalkane (HFA) propellants such as HFA-134a and HFA-227. Cosolvents have been added to medicinal formulations as one approach to addressing and overcoming this problem. Another approach avoids the use of cosolvents and provides sufficient amounts of surfactants in a medicinal formulation by the use of specific materials that are soluble in HFA propellants and are effective surfactants or dispersing aids in an aerosol formulation. Among such materials are certain fluorinated surfactants and certain polyethoxy surfactants.

Materials used in medicinal aerosol formulations that are delivered into the lungs are preferably non-toxic (e.g., "biocompatible") and are readily metabolized or eliminated from the body over time (e.g., "biodegradable"). Biocompatible and biodegradable polymers generally comprise a class of materials useful in the delivery of drugs to the lungs as well as to other areas of the body. For example, polymeric esters of selected hydroxycarboxylic acids or their derivatives (e.g., lactic acid, glycolic acid, p-dioxanone, etc.) are both biocompatible and biodegradable in the human body. These polymeric esters degrade over time into their constituent hydroxycarboxylic acids that can then be metabolized and naturally eliminated from the body. Biocompatible polymers have been used as solubilizing and/or stabilizing aids as well as vehicles for the delivery and sustained or controlled release of drugs. Such biocompatible polymers have been used in the formulations of certain drugs dispensed by MDIs into the lungs. While their use has been beneficial, the manufacture of biocompatible polymers has not been problem free. For example, certain acylated polymeric hydroxycarboxylic acids have proven to be useful in formulations dispensed through MDIs. But, the process for manufacturing such acylated polyhydroxycarboxylic acids also generates side products that can destabilize the polymer.

The manufacture of acylated polymeric hydroxycarboxylic acids is accomplished via a reaction between a polyhydroxycarboxylic acid and a suitable anhydride. However, the reaction also generates a mixed anhydride (e.g., anhydride formed between the terminal acid of a polymeric hydroxycarboxylic acid and another carboxylic acid group). In the past, the mixed anhydride has been hydrolyzed with added water. But, the hydrolysis reaction can be difficult to control and has been known cause hydrolysis of ester bonds along the length of the polymer chain resulting in the generation of additional non-acylated polyhydroxyacid comprising its own acid hydroxyl groups which tends to destabilize the biopolymer. The presence of these reactive hydroxyl groups can lead to further undesired side products.

It is desirable to provide medicinal compositions such as those comprising stable biocompatible polymer formulations. It is also desirable to provide methods for the manufacture of such medicinal compositions wherein the method for the manufacture of the medicinal compositions further minimize the potential for the creation of undesired reaction products.

SUMMARY OF THE INVENTION

The present invention provides methods for the manufacture of medicinal compositions. In some embodiments, the invention provides a method for the manufacture of a medicinal composition comprising:

(a) Providing a biocompatible polymer of the general formula

—[O—R$^1$—C(O)]$_n$— wherein:

"R$^1$" is a linear, branched, or cyclic organic group,

"n" is at least three, (b) Acylating the biocompatible polymer to provide an acylated biocompatible polymer and a mixed anhydride;

(c) Reacting the mixed anhydride with a nucleophile to provide an acylated biocompatible polymer with a terminal carboxylic acid derivative capable of being chemically converted to an acid in the absence of water;

(d) Converting the terminal carboxylic acid derivative to an acylated biocompatible polymer with a terminal carboxylic acid; and (e) Combining the acylated biocompatible polymer with a drug to provide the medicinal composition.

In other embodiments, the invention provides a method for the manufacture of a medicinal composition comprising:

(a) Providing a biocompatible polymer comprising oligolactic acid;

(b) Acylating the biocompatible polymer to provide acyl oligolactic acid and a mixed anhydride;

(c) Reacting the mixed anhydride with a tertiary alcohol in the absence of water to provide an ester that can be chemically converted to an acylated acid comprising acyl oligolactic acid, the alcohol having at least one hydrogen in the alpha position;

(d) Converting the ester to acyl oligolactic acid; and (e) Combining the acyl oligolactic acid with a drug to provide the medicinal composition.

In still other embodiments, the invention provides a method for the manufacture of a medicinal composition comprising:

(a) Providing a biocompatible polymer comprising oligolactic acid;

(b) Acetylating the biocompatible polymer to provide acetyl oligolactic acid and a mixed anhydride of acetyl oligolactic acid and acetic acid;

(c) Reacting the mixed anhydride with a tertiary alcohol to provide an ester that can be chemically converted to an acid comprising acetyl oligolactic acid in the absence of water;

(d) Converting the ester to acetyl oligolactic acid; and (e) Combining the acetyl oligolactic acid with a drug to provide the medicinal composition.

Examples of drugs that may be used include antiallergics, analgesics, bronchodilators, antihistamines, antiviral agent, antitussives, anginal preparations, antibiotics, antiinflammatories, immunomodulators, 5-lipoxygenase inhibitors, leukotriene antagonists, phospholipase A 2 inhibitors, phosphodiesterase IV inhibitors, peptides, proteins, steroids, vaccine preparations and combinations of any two or more of the foregoing. Particular drug examples include adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentamidine isoethionate, pirbuterol, prednisolone, salmeterol, terbutaline, tetracycline, 4-amino-α,α,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea and pharmaceutically acceptable salts and solvates thereof, and combinations of any two or more of the foregoing. Drugs of particular interest include beclomethasone dipropionate, butixocort propionate, pirbuterol, 4-amino-α,α,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and combinations of any two or more of the foregoing.

Certain terms used in the description of the embodiments of the invention shall be understood to have the following meanings:

The terms "polymer" and "polymeric" are, unless otherwise indicated, intended to broadly include homopolymers and block/random copolymers having a chain of at least three or more monomer structural units formed by polymerization reactions (e.g., condensation or ring-opening polymerization). The terms "oligomer" and "oligomeric" are used to refer to a subset of lower molecular weight polymers.

"Biocompatible polymer" refers generally to a polymer that is tolerated when placed within the body without causing significant adverse reactions (e.g., toxic or antigenic responses).

"Biodegradable polymer" refers to a polymer that degrades under biological conditions.

"Biological half-life" refers to the time required for half the mass of the material to disappear from the original site in vivo.

"Mixed anhydride" refers to an anhydride formed by reaction between an acylated biocompatible polymer of the type described herein and a carboxylic acid.

"Polydispersity" refers to the ratio of the weight-average to number-average molecular weights for a particular polymer.

Those skilled in the art will more fully appreciate the various features of the present invention upon consideration of the remainder of the disclosure including the various Figures, the Detailed Description Of The Preferred Embodiment including the Examples and the appended claims.

BRIEF DESCRIPTION OF THE DRAWINGS

The description of the preferred embodiment of the invention is made with reference to the Figures, wherein.

DETAILED DESCRIPTION OF THE PREFERRED EMBODIMENT

Figure 1:
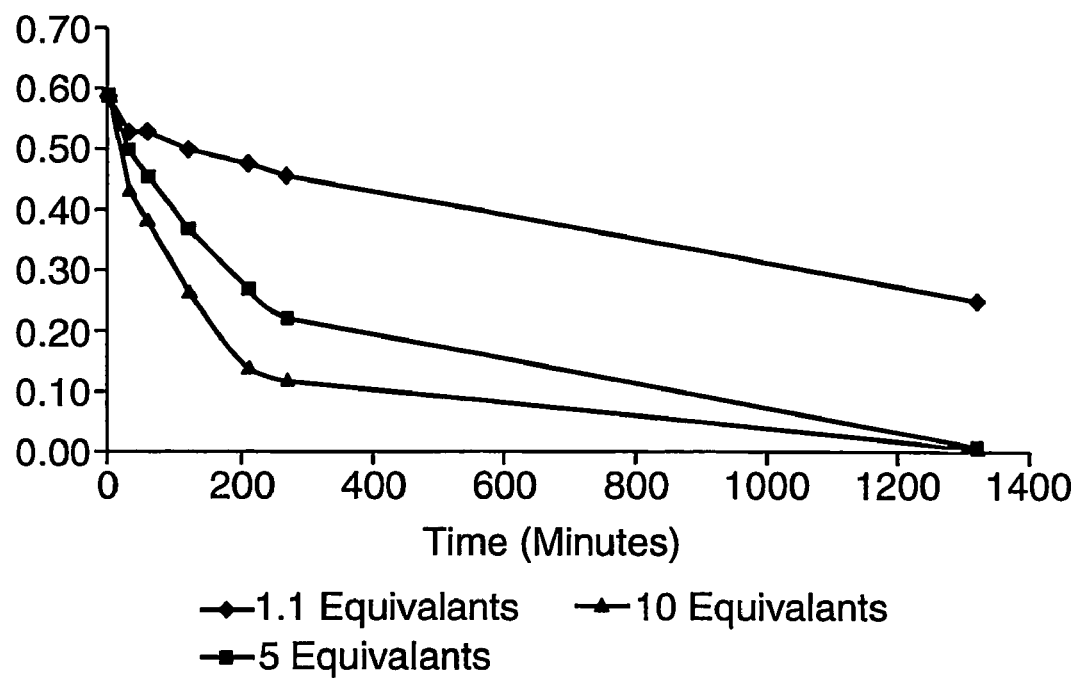
FIG. 1 is a plot of ratio of the integrated area of nmr peaks as a measure of the mole fraction of certain components in a sample over time as is described in Example 1.

The present invention provides methods of manufacturing compositions comprising compounds (or dispersing aids) and one or more drugs. Compounds for use in the invention comprise at least one polymeric or oligomeric chain which can be linear, branched, or cyclic. The compounds may optionally comprise one or more of: an ionic group; a group that contains one or more hydrogen atoms capable of hydrogen bonding; or a group containing no hydrogen atoms capable of hydrogen bonding.

The polymer chain comprises units derived from any of a hydroxyacid, amino acid, or mercapto acid. The chains can be homopolymer chains (i.e., those derived from a single such acid) or copolymer chains (e.g., chains containing randomly distributed units or blocks of units derived from any two or more such acids). As the terminology is used herein, a chain may be referred to as "derived from" a particular precursor without necessarily having been prepared from that precursor if the chain has a chemical structure that is consistent with that which could have been obtained from a particular precursor.

A precursor hydroxyacid can be any hydroxyacid, e.g., a hydroxycarboxylic acid, or the corresponding lactone or cyclic carbonate, if any. It is preferred that the hydroxyacid be endogenous to the human body. Suitable hydroxycarboxylic acids include straight chain (e.g., $C_2$ to $C_6$) hydroxyalkyl carboxylic acids such as hydroxyacetic acid, hydroxypropionic acids (e.g., 2- or 3-hydroxypropionic acid), hydroxybutyric acids (e.g., 2-, 3-, or 4-hydroxybutyric acid), hydroxyvaleric acids (e.g., 2-, 3-, 4-, or 5-hydroxyvaleric acid), hydroxycaproic acids (e.g., 2-, 3-, 4-, 5-, or 6-hydroxycaproic acid), branched chain $C_3$ to $C_6$ hydroxyalkyl carboxylic acids (e.g., 2-hydroxydimethylacetic acid), malic acid monoesters, and the like. Suitable lactones include lactides, 1,4-dioxanone, valerolactone, and caprolactone. Suitable cyclic carbonates include trimethylene carbonate. Units derived from a hydroxycarboxylic acid can be designated by the general formula

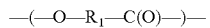

wherein $R_1$ designates an organic moiety that functions to link the heteroatom terminus (in this case —O—) to the carbonyl terminus

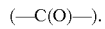

$R_1$ is preferably straight chain, branched chain, or cyclic alkylene or alkenylene, preferably containing from one to about six carbon atoms. When $R_1$ is alkylene or alkenylene it can also contain heteroatomic functional groups such as carbonyl, oxy, thio, or catenary nitrogen, preferably fully substituted catenary nitrogen wherein the substituent is free of hydrogen-donor hydrogen bonding functional groups. $R_1$ preferably contains one to about four catenary atoms. $R_1$ can also be arylene (e.g., 1,4-phenylene) or arylene substituted by functional groups that do not contain hydrogen atoms capable of hydrogen bonding, e.g., lower alkyl or lower alkoxy. The term "lower" when used in connection with alkyl, alkenyl, alkoxy, alkenylene, or alkylene groups refers to such groups having one to about four carbon atoms. $R_1$ can also be a combination of such arylene, alkenylene, and alkylene groups, such as 1,4-xylylene.

A precursor amino acid can be any compound having an amino group, preferably a secondary amino group, at least one carbon atom removed from an acid group such as a carboxylic acid group. Exemplary amino acids include secondary amino acids (sometimes referred to as "imino acids") such as sarcosine and proline. As with the hydroxyacids discussed above it is preferred that the aminocarboxylic acid be endogenous to the human body.

A unit derived from an amino acid can be designated by the general formula

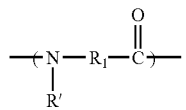

wherein $R_1$ is as defined above and R' is hydrogen or a group other than hydrogen, preferably a group that is free of hydrogen-donor hydrogen bonding functional groups. Exemplary suitable groups that can be bonded to the imino nitrogen include alkyl, alkoxyalkyl, haloalkyl, phenylalkyl, alkenyl, haloalkenyl, phenyl, alkylphenyl, alkoxyphenyl, halophenyl, and others readily selected by those skilled in the art. In certain embodiments, the alkyl, alkoxy, or alkenyl moieties in these functional groups may contain from one to about eighteen, in other embodiments from one to about six carbon atoms. Most typically they are lower alkyl, alkoxy, or alkenyl groups.

A precursor mercapto acid can be any compound comprising a thiol group and an acid group such as a carboxylic acid group. Exemplary mercapto acids include 2-mercaptopropionic acid, 3-mercaptopropionic acid, and mercaptoacetic acid. A unit derived from a mercaptocarboxylic acid can be designated by the general formula

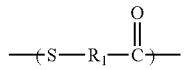

wherein $R_1$ is as defined above.

It is within the skill of those practicing in the art to select units for inclusion in the chains of the compounds of the dispersing aid described above, giving due consideration to factors that affect dispersing aid function or suitability for inhalation including ease of metabolism, solubility, crystallinity, structural homogeneity, molecular weight, degree of branching, relative amount of polar and non-polar portions of the chain, the particular propellant to be used in connection with the dispersing aid, and the particular drug to be included in the formulation. For example, certain homopolymer chains or chains having excess aromatic content can be excessively crystalline and unsuitable for use with HFA propellants. The use of minor amounts (e.g., 10 to 40 mole percent) of "comonomers" or the use of an enantiomeric mixture of a chiral monomer can serve to render a material more amorphous. Likewise, excessive hydrogen bonding can interfere with dispersing aid function but is readily avoided by selecting appropriate chain components.

The term "chain length" as used herein denotes the average number of monomer units in the chain. Generally chains contain a plurality of the above-described units. Chain length is generally less than 100, in some embodiments between about 3 and about 70, and in other embodiments between about 3 and about 40, and in still other embodiments between about 3 and about 14. Particular chain lengths will depend on certain of the factors discussed above. Relatively short chain lengths (e.g., from six to twelve units) may be desired in some applications because they might be expected to be more readily metabolized than materials having greater chain lengths. Lactic acid based dispersing aids, for example, may comprise chain lengths of about four or more, especially if used with HFA-227, while chain lengths of about six or more are more typical for use with HFA-134a.

While polymers contain a distribution of chain lengths, certain chain length components can be removed from the distribution such as components having a chain length of less than three. The removal of short chain length components will raise the average chain length "n" of a given dispersing aid composition. Additionally, excessive crystallinity may be a problem in some dispersing aids and may benefit from the removal of the higher molecular weight fraction.

The compound contains at least one chain as described above. In certain embodiments the compound contains two or more such chains arranged, e.g., as described below in connection with divalent and polyvalent capping groups. A chain can be capped at one end or both ends by a monovalent, divalent or polyvalent organic moiety (each valence of the capping group being independently bonded to a chain) that does not contain hydrogen atoms capable of hydrogen bonding. Such groups are well known and can be readily selected by those skilled in the art, and the particular structure of such a group may be determined by factors relating to synthetic expediency (as discussed below in connection with preparation of the dispersing aid) such as, for example, whether a carbonyl terminus or a heteroatom terminus of a chain is capped by a particular group. Exemplary monovalent organic moieties for capping the heteroatom terminus of a chain include organocarbonyl groups such as those of the formula $$R_2—C(O)—$$

wherein $R_2$ is straight chain, branched chain, or cyclic alkyl optionally containing heteroatomic functional groups such as carbonyl, oxy, thio, or catenary nitrogen, possibly containing from one to about eighteen carbon atoms, and typically containing one to about six carbon atoms, phenyl, or phenyl substituted by one or more lower alkyl, lower alkoxy, or halogen groups. Groups of the formula —$R_2$ are also suitable. Other suitable monovalent organic moieties, particularly for capping the carbonyl terminus of a chain, include those of the formula —$OR_2$, —$SR_2$, or —$N(R_2)_2$ wherein $R_2$ is as defined above.

In embodiments that comprise two or more chains, the groups that cap the chains (the capping groups) can be identical to or different from one another. Furthermore in such embodiments the capping groups need not terminate the compound but can be divalent or polyvalent groups that bridge two or more chains. Exemplary bridging groups (which are a subgenus of capping groups) include straight chain, branched chain, or cyclic alkylene groups optionally containing heteroatomic functional groups such as carbonyl, oxy, thio, or catenary nitrogen. Groups derived from dihydridic alcohols such as polyethylene glycol [i.e., groups of the formula —(—$OCH_2CH_2$—)$_n$—O or —(—$OCH_2CH_2$—)$_n$— wherein n is an integer greater than one], polypropylene glycol [i.e., groups of the formula —($OCH(CH_3)CH_2$—)$_n$—O or —$OCH(CH_3)CH_2$—)$_n$ wherein n is an integer greater than one] are suitable. Also suitable are groups derived from polyhydric alcohols, such as 1,2,3-trioxypropane (derived from glycerol) and polyvalent groups such as those of the formula

and the like. Bridging groups for bridging between heteroatom termini include those of the formula

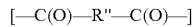

wherein R" is straight chain, branched chain, or cyclic alkylene or alkenylene optionally containing heteroatomic functional groups such as carbonyl, catenary nitrogen, oxy, or thio, and preferably containing from one to about eighteen carbon atoms, phenylene, or phenylene substituted by one or more lower alkyl, lower alkoxy, or halogen groups.

The chain may also be bonded at one end or both ends to a moiety that contains an ionic group or a group that contains hydrogen atoms capable of hydrogen bonding. Suitable ionic groups include, for example, quaternary ammonium groups, sulfonate salts, carboxylate salts, and the like. Hydrogen, when bonded to the heteroatom terminus of a chain, is capable of hydrogen bonding. Other suitable groups that contain hydrogen atoms capable of hydrogen bonding include acid functional groups, amides, carbamates, and groups such as amino, hydroxyl, thiol, aminoalkyl, alkylamino, hydroxyalkyl, hydroxyalkylamino, sugar residues, and the like. The suitability of any particular group for use in connection with a particular chain will depend upon the structure of the respective group and chain. For example, in a polyhydroxy-carboxylic acid-derived chain, primary or secondary amino groups are typically protonated in order to avoid nucleophilic displacement within the chain by an amino group.

Suitable acid functional groups include carboxylic acid. Other suitable moieties that contain acid functional groups include α-amino acid residues or esters thereof. In one such embodiment the amino group of the α-amino acid is bonded to a carbonyl terminus of the chain. In such embodiments preferred α-amino acid residues include those of the formula

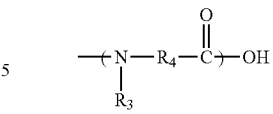

wherein $R_3$ is hydrogen and $R_4$ is straight chain, branched chain, or cyclic alkylene containing one catenary carbon atom and a total of one to about 12 carbon atoms, optionally substituted by one or more of lower alkoxy, lower alkylthio, carboxy, mercapto, hydroxy, phenyl, hydroxyphenyl, indolyl, guanidinyl, carbamido (i.e., —$NHC(O)NH_2$), imidazolyl, or acylamino (i.e., —$C(O)NH_2$), or wherein $R_3$ and $R_4$ together form a straight chain butane-1,1,4-triyl group optionally substituted by hydroxy. In embodiments wherein the amino acid residue contains a nucleophilic group such as hydroxy or mercapto, the amino group can be blocked, e.g., by an acetyl group, and the carbonyl terminus of a chain can be bonded to the amino acid residue via the nucleophilic —S— or —O— atom of the amino acid.

In another embodiment the α-amino acid residue is bonded to the heteroatom terminus (e.g., to an —O—, —S—, or —NR'— group) of the chain and is of the formula

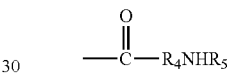

wherein $R_4$ is as defined above and $R_5$ is hydrogen or a blocking group such as organocarbonyl (e.g., acetyl) as defined above.

Amino acid residues suitable for inclusion herein are those that are derived from endogenous amino acids or esters thereof such as glycine, alanine, valine, leucine, isoleucine, serine, threonine, phenylalanine, tyrosine, tryptophan, cysteine, methionine, aspartic acid, glutamic acid, asparagine, glutamine, lysine, hydroxylysine, arginine, citrulline, histidine, proline, and hydroxyproline. Taurine, α,β-amino sulfonic acid, is also suitable.

As with the above-described capping groups, the moiety containing an ionic or hydrogen bonding group need not terminate the compound; rather it can be a divalent or polyvalent group bridging the chains. Exemplary groups of this type include alkylene diimino groups and polyoxyalkylene-diimino groups.

The dispersing aid may be soluble in a propellant composition comprising a hydrofluorocarbon, such as HFA-134a (1,1,1,2-tetrafluoroethane) or HFA-227 (1,1,1,2,3,3,3-heptafluoropropane) in an amount effective to stabilize a suspension aerosol formulation. The amount that constitutes such an effective amount may depend on certain factors such as the particular dispersing aid (e.g., the hydroxyacid from which the chain is derived, the chain length, the presence or absence of terminal and capping groups), the particular propellant, the particular drug in the formulation, and the physical form of the drug (e.g., the particle size of the drug). Such effective amounts can be readily determined by those skilled in the art with due consideration of the factors discussed above.

Some embodiments of the dispersing aid may include polymer chains comprising units derived from lactic acid, glycolic acid, trimethylene carbonate, polyhydroxybutyrate, or p-dioxanone. In embodiments where the lactic acid unit is the only component of the chain, the chain may comprise at least about 3 units and typically from about 3 units to about 40 units. Lower chain lengths (e.g., from six to twelve) are more typical inasmuch as the chains could be expected to be more readily metabolized than longer chain length materials. Also in such embodiments; the chain may be capped at one end as described above, such as by an organocarbonyl group, and typically by an acetyl group.

Another embodiment comprises units derived from glycolic acid (i.e., units of the formula —OCH$_2$C(O)—) and units derived from lactic acid. In such embodiments the chain may contain a total of 3 to about 40 units. Also in such embodiments the chain may be capped at one end as described above, such as by an organocarbonyl group or an acetyl group.

A medicinal aerosol formulation of the invention may comprise a dispersing aid as described above. A single dispersing aid such as, for example a substantially monodisperse material, may be used. Also, a combination of one or more dispersing aids can be used such as by combining two dispersing aids comprising the same constituent monomers but having different chain lengths, or combining two or more dispersing aids containing different constituent monomers or capping groups. A single dispersing aid may also have a distribution of different chain lengths comprising the same constituent monomers, that is, a single dispersing aid may be polydisperse.

An aerosol formulation will typically comprise a dispersing aid, as described herein, in an amount effective to stabilize the formulation compared to an identical formulation not containing the dispersing aid. In this manner, the formulation is stabilized so that the drug does not settle, cream, or flocculate after agitation so quickly as to prevent reproducible dosing of the drug. Reproducible dosing can be achieved if the formulation retains a substantially uniform drug concentration for about two or three seconds after agitation.

The particular amount of dispersing aid that constitutes an effective amount is dependent upon the particular dispersing aid, the particular propellant, and on the particular drug used in the formulation, and such amounts can readily be determined by those skilled in the art without undue experimentation. In general, the dispersing aid can be present in a medicinal formulation in an amount from about 0.001 to about 1 part by weight, in some embodiments from about 0.01 to about 0.25 parts by weight, based on 100 parts by weight of the propellant.

The formulations of the invention contain a drug in a therapeutically effective amount such that the drug can be administered as an aerosol (e.g., topically or by oral or nasal inhalation) and provide a desired therapeutic effect with one dose or less, but possibly requiring several doses. The aerosol formulations of the invention can be dispensed with a conventional valve, e.g., a metered dose valve. The amount of a drug that constitutes a therapeutically effective amount will depend on the nature of the drug, its potency, the route of administration of the formulation, and the mechanical system used to administer the formulation. A therapeutically effective amount of a particular drug can be selected by those of ordinary skill in the art with due consideration of such factors. In general, a therapeutically effective amount of a drug will range from about 0.02 parts by weight to about 2 parts by weight based on 100 parts by weight of the propellant.

The drug may be micronized, especially in formulations of the invention intended for inhalation into the lungs. In a micronized formulation, a therapeutically effective fraction of the particles (e.g., about 90 percent or more) will typically have a diameter of less than about 10 microns. The small size of the particles is desired to assure that the particles can be inhaled into the respiratory tract and/or lungs. Suitable drugs for use in a medicinal formulation of the invention include any drug suitable for administration by inhalation. Therapeutic categories include antiallergics, analgesics, bronchodilators, antihistamines, antitussives, anginal preparations, antibiotics, antiinflammatories, peptides, proteins, and steroids. Particular drugs include albuterol, atropine, beclomethasone, budesonide, cromolyn, epinephrine, ephedrine, fentanyl, flunisolide, formoterol, ipratropium bromide, isoproterenol, pirbuterol (e.g., pirbuterol acetate), prednisolone, salmeterol, and pharmaceutically acceptable salts and solvates thereof.

Suitable propellants for inclusion in the aerosol formulations of the invention include conventional chlorofluorocarbon (CFC) propellants such as mixtures of propellants 11, 12, and 114. Non-CFC propellants, particularly 1,1,1,2-tetrafluoroethane (Propellant 134a), 1,1,1,2,3,3,3-heptafluoropropane (Propellant 227), or mixtures thereof, are also suitable. The propellant is typically present in an amount sufficient to propel a plurality of doses of drug from an aerosol canister. Further components, such as conventional lubricants or surfactants, cosolvents (e.g., ethanol), and the like, can also be present in an aerosol formulation of the invention in amounts readily determinable by those skilled in the art.

Dispersing aids for use in medicinal formulations of the invention can be prepared as set forth in the reaction scheme described below. The reaction scheme illustrates hydroxyacid-derived compounds. Other compounds, such as amino acid-derived compounds and mercapto acid derived compounds, can be prepared by those skilled in the art using well known methods of functional group protection and manipulation in variants of the illustrated reactions. Furthermore, many acid-derived compounds other than those illustrated in the reaction scheme can be prepared or otherwise obtained by those skilled in the art.

Step (i) typically involves condensing a hydroxyacid (e.g., a hydroxycarboxylic acid) to provide a biocompatible polyhydroxyacid. The condensation can be carried out under conventional reaction conditions such as by heating the hydroxyacid, optionally in an aprotic solvent, typically at a temperature sufficient to remove by distillation the water produced by the reaction to produce the biocompatible polyhydroxyacid. The polymer chain length can be controlled in a known manner by controlling the time and temperature of the reaction.

In step (ii) a biocompatible polyhydroxyacid made according to step (i) is typically capped at the oxy terminus by reacting with a compound containing an activated acyl group, e.g., an acid anhydride such as acetic anhydride, to provide a biocompatible acyl polyhydroxyacid. A biocompatible acyl polyhydroxyacid is compatible with and often soluble in certain propellants useful in the formulation of medicinal compositions. The acyl polyhydroxyacid can be used as a dispersing aid without further elaboration. However, a mixed anhydride is often created during step (ii) as an undesired side product of acylation. While the mixed anhydride can be hydrolyzed in the presence of water, the use of water can generate additional non-acylated compounds comprising unreacted hydroxy end groups (e.g., polyhydroxyacid), and the presence of these hydroxyl groups can destabilize the biocompatible acyl polyhydroxyacid as well as the medicinal formulations which incorporate the acyl polyhydroxyacid. The present invention avoids the creation of undesired hydroxy functionality and the problems associated therewith by avoiding the addition of water to hydrolyze the mixed anhydride.

Therefore, step (iii) involves the reaction of the mixed anhydride with a compound that provides a protected carboxylic acid that can be converted to the free carboxylic acid by a non-hydrolytic process. In some embodiments, a suitable protecting group may comprise, for example, a tertiary alcohol having at least one hydrogen in the alpha position. In this step, one or more suitable alcohols are added to the mixture of acylated polyhydroxyacid/mixed anhydride to form an ester of the acylated polyhydroxyacid. The ester may be characterized in that it can be chemically converted to an acid in the absence of water. Suitable alcohols for use in the formation of the foregoing ester include any of a variety of tertiary alcohols having at least one hydrogen in the alpha position. Specific examples of such alcohols include without limitation, t-butanol, derivatives of t-butanol, and combinations of two or more of the foregoing. The resulting tertiary esters can be converted to the acylpolyhydroxy acid by acid catalyzed or thermolytic elimination of isobutylene or an isobutylene derivative. Other nucleophilic alcohols include benzyl alcohol and its derivatives (e.g. p-nitrobenzyl alcohol) which result in esters that can be converted to the acylpolyhydroxy acid by hydrogenation, 2,2,2-trichloroethanol or its derivatives which result in esters that can be converted to the acylpolyhydroxy acid by reaction with zinc or electrolysis and allyl alcohol or its derivatives which result in esters that can converted to the acylpolyhydroxy acid by palladium catalyzed allyl transfer.

Step (iv) provides cleavage of the ester group from the reaction of nucleophilic alcohol and the acylated polyhydroxyacid. Any of several reactions may be used in this step (iv) to cleave the ester and chemically convert the ester to an acid in the absence of water, thereby providing a relatively pure acylated polyhydroxyacid. Suitable methods for the conversion of the ester are dependent on the chemical nature of the ester and include catalytic hydrogenation using hydrogen gas, acid catalysis, heating the ester to a reflux temperature for a suitable period of time or other non-hydrolytic methods as described above. By providing the acylated polyhydroxyacid in the absence of added water, the potential for undesired hydrolysis of the polymer is minimized and the formation of unwanted hydroxyl groups along the hydrolyzed polymer is avoided. In this manner, a stable form of the acyl polyhydroxyacid is easily obtained and the medicinal formulations in which the polymer is dispersed or dissolved will also be of enhanced stability.

Exemplary of the foregoing process involves the use oligolactic acid (OLA) as the biocompatible polyhydroxyacid, acetic anhydride to provide acyl functionality and t-butanol as the tertiary alcohol used in accomplishing step (iii). Step (i) is a condensation reaction with lactic acid to provide OLA. Accordingly, step (ii) comprises the reaction of OLA with acetic anhydride to provide acetyl OLA and a mixed anhydride of acetyl OLA and acetic acid. This may be accomplished in the presence of an added solvent (e.g., ethyl acetate) or the reaction may conveniently be performed "neat." In step (iii), the mixed anhydride is reacted with t-butanol to provide the t-butyl ester of acetyl OLA. The ester is converted to the carboxylic acid (by elimination of isobutylene) in step (iv), either by acid catalysis or by the application of heat (e.g., heating to 150° C. for a period of 6-16 hrs under vacuum). The resulting reaction mixture comprises acetyl OLA and isobutylene, which is removed by volatilization during the process, in addition to residual tertiary butanol and tertiary butylacetate, which can be removed during subsequent purification by evaporative processes. The foregoing reaction sequence can be represented as follows:

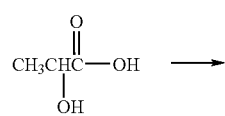

(i)

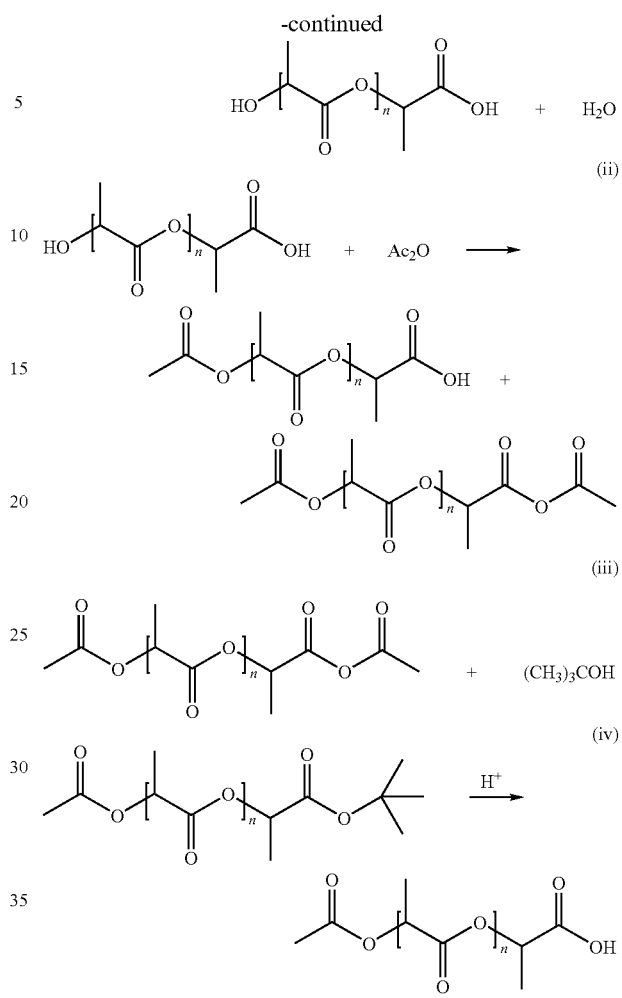

It will be appreciated that changes to the reaction scheme may be made for any of a variety of reasons such as the desire to render the process more efficient, reducing components costs, and the like. In one variation of the foregoing process, changes may be made to some of the reactant components used in the various process steps which may additionally require changes in reaction conditions or the like. For example, when benzyl alcohol is used in place of t-butanol, it may be desirable to convert the ester in step (iv) to the carboxylic acid by reaction with hydrogen using any of a variety of known hydrogenation catalysts. Likewise, the above described reaction scheme may be performed under different conditions than those mentioned or with components that differ from the specific components described herein. Different alcohols, different polyacids, and simple or complex derivatives of the described components may be readily substituted into the reaction scheme by those skilled in the art, and the present invention is to be construed to encompass such variations.

It may be desirable to incorporate an amino acid residue into the biocompatible polymers described herein. To do so, the acyl capped product of step (iv), which still possesses a carboxylic acid group, can be converted by activating the carboxylic acid and reacting with an amino acid. The carboxylic acid is activated (e.g., converted to the corresponding acid halide) by methods known to those skilled in the art, such as by reacting with a carboxy activating reagent (e.g., ethylchloroformate, oxalyl chloride, POCl₃, SOCl₂, or the like). The acid halide may then be reacted with the amino acid to thereby incorporate the amino acid into the polymer. Other carboxylate activating groups can also be used (e.g. carbodiimides, carbonyl diimidazole, and others known to those skilled in the art).

The molecular weight distribution of a biocompatible polymer can be adjusted and optimized by using methods known to those skilled in the art. Generally the dispersing aid can be fractionated by distillation or precipitation in order to provide a desired distribution. For example, low molecular weight species can be readily removed by molecular distillation. With lactic acid based dispersing aids, low molecular weight species (e.g., n=1, 2, or 3) can be removed by extracting with water prior to step (ii) of the reaction scheme described herein.

Medicinal formulations of the invention can be prepared by combining (i) the drug in an amount sufficient to provide a plurality of therapeutically effective doses; (ii) the biocompatible polymer or dispersing aid; (iii) the propellant in an amount sufficient to propel a plurality of doses from an aerosol canister; and (iv) any further optional components; and dispersing the components. The components can be dispersed using a conventional mixer or homogenizer, by shaking, by ultrasonic energy, or the like. Bulk formulation can be transferred to smaller individual aerosol vials by using valve to valve transfer methods or by using conventional cold-fill methods. It is not required that a dispersing aid used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular dispersing aids and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFA-134a or HFA-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as those disclosed in commonly assigned U.S. Pat. No. 5,836,299 to Kwon. Also suitable are diaphragms fashioned by extrusion, injection molding or compression molding from a thermoplastic elastomeric material such as those disclosed in U.S. Pat. No. 5,290,539 to Marecki.

Conventional aerosol canisters, e.g., those of aluminum, glass, stainless steel, or polyethylene terephthalate, can be used to contain a medicinal formulation of the invention.

Medicinal formulations of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, or diabetes, or they can be delivered via topical (e.g., buccal) administration in order to treat, e.g., angina or local infection.

EXAMPLES

The following non-limiting Examples are provided to illustrate embodiments of the invention. All parts and percentages are by weight unless otherwise indicated.

Example 1

Oligolactic acid was made by heating D,L-lactic acid under vacuum at 150° C. until the desired degree of oligomerization was reached, as measured by NMR. The oligolactic acid was cooled to 100° C. and approximately one weight equivalent of acetic anhydride was added. This solution was heated at 100° C. for 16 hr. Excess acetic anhydride and acetic acid was removed by distilling them from the acetylated oligolactic acid. The acetyloligolactic acid (n=10.4 by NMR, 76 grams) was dissolved in approximately 150 ml ethyl acetate and divided into three equal aliquots. Each aliquot was purged with nitrogen and heated to reflux. A sample was taken, the ethyl acetate was removed under reduced pressure and the sample further dried under high vacuum for approximately 30 seconds. The residue was dissolved in CDCl₃ and analyzed by NMR. The presence of several acetyl peaks was evident and were identified by comparison to reference spectra or standards.

Alcohol (t-butanol) was added to each of the three aliquots in amounts equal to 1.1, 5 and 10 molar equivalents to the OLA. Heating at reflux was continued and samples were taken at various intervals. The samples were concentrated as described above and analyzed by NMR. The NMR peaks were integrated and the ratio of the area of the peaks between $\delta$=2.7-2.9 to the peak at 2.13 was calculated to provide a measure of the mole fraction of mixed anhydride (assuming complete acetylation of the terminal —OH group). A plot of this ratio versus time is shown in FIG. 1.

After 22 hours, the mixed anhydride was not detectable by NMR when 5 and 10 equivalents of t-butanol was used. The formation of the t-butyl ester of OLA was observed by NMR.

Example 2

Figure 2:
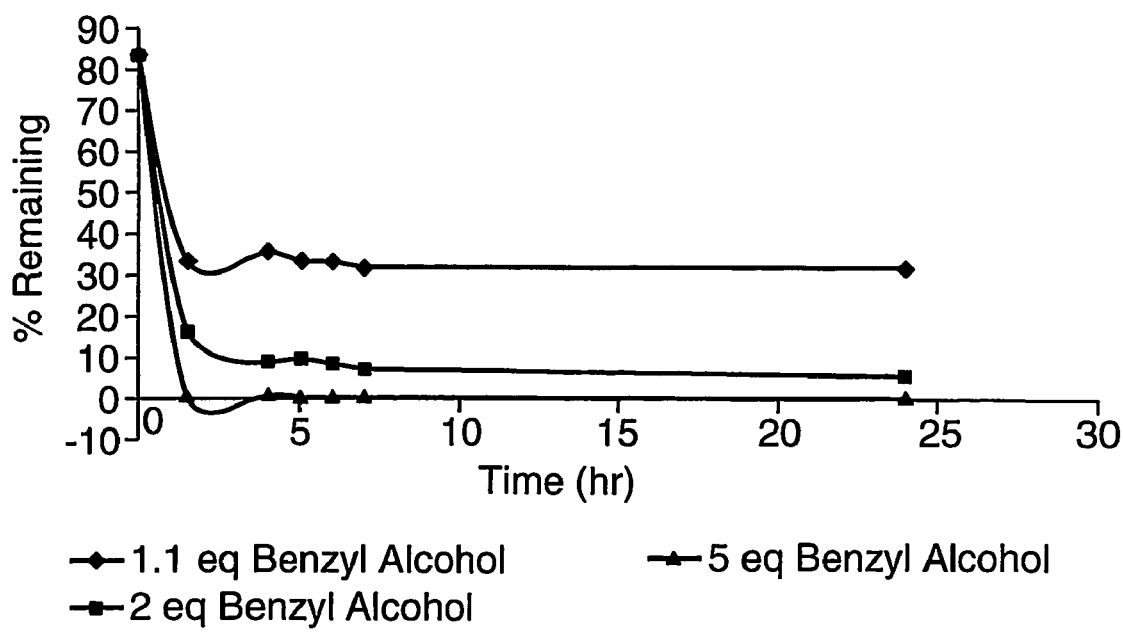
FIG. 2 is a plot of ratio of the integrated area of nmr peaks as a measure of the mole fraction of certain components in a sample over time as is described in Example 2.

Acetyloligolactic acid was made as described in Example 1. The acetyloligolactic acid (n=7.9 as measured by NMR) was dissolved in approximately 150 ml ethyl acetate and divided into three equal aliquots. Each aliquot was purged with nitrogen and heated to reflux. A sample was taken from each aliquot, the ethyl acetate solvent was removed under reduced pressure and the sample further dried under high vacuum for approximately 30 seconds. The residue was dissolved in CDCl₃ and analyzed by NMR as described in Example 1. Benzyl alcohol was added to the three aliquots in amounts equal to 1.1, 2 and 5 molar equivalents to the OLA. Heating at reflux was continued and samples taken at various time points, concentrated as described in Example 1 and analyzed by NMR. The peaks were integrated and the ratio of the area of the peaks between $\delta$=2.7-2.9 to the peak at 2.13 was calculated. The ratio was taken as a measure of the mole fraction of mixed anhydride (assuming complete acetylation of the terminal —OH group). A plot of this ratio versus time is shown in FIG. 2.

After four hours, the mixed anhydride was not detectable by NMR using 5 equivalents of benzyl alcohol. The formation of the benzyl ester of OLA was observed on the NMR.

Example 3

80% D,L-lactic acid in H₂O (2.0 kg, Wilke International, Lenexa, Kans.) was oligomerized by heating in a roundbottom flask at 150° C. under vacuum (10-50 mm Hg) until the desired level of oligomerization was reached (n=20.6, as measured by NMR). The reaction was cooled to 80° C. and 0.8 kg acetic anhydride (Aldrich Chemical Company, Milwaukee, Wis.) was added. The acetylation reaction was continued at ambient pressure under an inert environment for 4 hrs. Excess acetic anhydride was removed under vacuum at 90° C. until distillation ceased. Tertiary butanol (0.5 kg, Aldrich Chemical Co., Milwaukee, Wis.) was then added and the solution heated at 90° C. for 4 hrs. Excess t-butanol was removed under vacuum at 120° C. The product was maintained under vacuum (5-8 mmHg) and heated at 150° C. for 4 hrs. Thermal breakdown of the tertiary butyl esters was confirmed by NMR analysis of the product.

While the invention has been described in terms of the embodiments for which an enabling description was available, it will be appreciated that insubstantial modifications of the invention, not presently foreseeable by those of reasonable skill in the art, may nonetheless represent equivalents thereto. All such unforeseeable modifications are to be considered within the scope of the present invention.

What is claimed:

1. A method for the manufacture of a medicinal composition comprising:
   (a) Providing a biocompatible polymer of the general formula $$—[O—R^1—C(O)]_n—$$

wherein:
   "$R^1$" is a linear, branched, or cyclic organic group,
   "n" is at least three,
   (b) Acylating the biocompatible polymer to provide an acylated biocompatible polymer and a mixed anhydride;
   (c) Reacting the mixed anhydride with a nucleophile to provide an acylated biocompatible polymer with a terminal carboxylic acid derivative capable of being chemically converted to an acid in the absence of water;
   (d) Converting the terminal carboxylic acid derivative to an acylated biocompatible polymer with a terminal carboxylic acid; and
   (e) Combining the acylated biocompatible polymer with a drug to provide the medicinal composition.

2. The method as defined in claim 1 wherein $R_1$ comprises a chain of one to about six carbon atoms.

3. The method as defined in claim 1 wherein $R_1$ is alkylene or alkenylene comprising heteroatomic functional groups.

4. The method as defined in claim 3 wherein the heteroatomic functional groups are selected from the group consisting of carbonyl, oxy, thio, catenary nitrogen and combinations of two or more of the foregoing.

5. The method as defined in claim 1 wherein $R_1$ comprises a lower alkyl or lower alkoxy.

6. The method as defined in claim 5 wherein $R_1$ is selected from the group consisting of alkyl, alkenyl, alkoxy, alkenylene, alkylene and combinations of two or more of the foregoing, wherein $R_1$ comprises from about one to about four carbon atoms.

7. The method as defined in claim 1 wherein providing the biocompatible polymer comprises the condensation of an acid to form the biocompatible polymer.

8. The method as defined in claim 7 wherein the acid is lactic acid and the biocompatible polymer is oligolactic acid.

9. The method as defined in claim 8 wherein acylating the biocompatible polymer comprises reacting the oligolactic acid with acetic anhydride to provide acetyl oligolactic acid; and wherein reacting the mixed anhydride with a nucleophile comprises reacting the mixed anhydride with a nucleophile selected from the group consisting of benzyl alcohol, t-butanol, derivatives of benzyl alcohol, derivatives of t-butanol and combinations of two or more of the foregoing.

10. The method as defined in claim 1 wherein the nucleophile is an alcohol selected from the group consisting of benzyl alcohol, t-butanol, derivatives of benzyl alcohol, derivatives of t-butanol and combinations of two or more of the foregoing.

11. The method as defined in claim 1 wherein the drug comprises a substance selected from the group consisting of antiallergics, analgesics, bronchodilators, antihistamines, antiviral agents, antitussives, anginal preparations, antibiotics, antiinflammatories, immunomodulators, 5-lipoxygenase inhibitors, leukotriene antagonists, phospholipase A 2 inhibitors, phosphodiesterase IV inhibitors, peptides, proteins, steroids, vaccine preparations and combinations of any two or more of the foregoing.

12. The method as defined in claim 1 wherein the drug comprises a substance selected from the group consisting of adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentamidine isoethionate, pirbuterol, prednisolone, salmeterol, terbutaline, tetracycline, 4-amino-α,α,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea and pharmaceutically acceptable salts and solvates thereof, and combinations of any two or more of the foregoing.

13. Method as defined in claim 1 wherein the drug comprises a substance selected from the group consisting of beclomethasone dipropionate, butixocort propionate, pirbuterol, 4-amino-α,α,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and combinations of any two or more of the foregoing.

14. The method as defined in claim 1 wherein the drug is in solution.

15. The method as defined in claim 1 wherein the drug is in suspension.

16. The method as defined in claim 15 wherein the drug comprises particles having a diameter of less than about 10 micrometers.

17. The method as defined in claim 1 wherein the medicinal composition is in a form that can be administered as an aerosol.

18. A method for the manufacture of a medicinal composition comprising:
   (a) Providing a biocompatible polymer comprising oligolactic acid;
   (b) Acylating the biocompatible polymer to provide acyl oligolactic acid and a mixed anhydride;
   (c) Reacting the mixed anhydride with a tertiary alcohol in the absence of water to provide an ester that can be chemically converted to an acylated acid comprising acyl oligolactic acid, the alcohol having at least one hydrogen in the alpha position;
   (d) Converting the ester to acyl oligolactic acid; and
   (e) Combining the acyl oligolactic acid with a drug to provide the medicinal composition.

19. The method as defined in claim 18 wherein acylating the biocompatible polymer comprises reacting the oligolactic acid with acetic anhydride to provide the acyl oligolactic acid comprising acetyl oligolactic acid and the mixed anhydride comprising a mixed anhydride of acetyl oligolactic acid and acetic acid; and wherein reacting the mixed anhydride with a nucleophile comprises reacting the mixed anhydride with a nucleophile selected from the group consisting of benzyl alcohol, t-butanol, derivatives of benzyl alcohol, derivatives of t-butanol and combinations of two or more of the foregoing.

20. The method as defined in claim 18 wherein the drug comprises a substance selected from the group consisting of antiallergics, analgesics, bronchodilators, antihistamines, antiviral agents, antitussives, anginal preparations, antibiotics, antiinflammatories, immunomodulators, 5-lipoxygenase inhibitors, leukotriene antagonists, phospholipase A 2 inhibitors, phosphodiesterase IV inhibitors, peptides, proteins, steroids, vaccine preparations and combinations of any two or more of the foregoing.

21. The method as defined in claim 18 wherein the drug comprises a substance selected from the group consisting of adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentamidine isoethionate, pirbuterol, prednisolone, salmeterol, terbutaline, tetracycline, 4-amino-$\alpha,\alpha$,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea and pharmaceutically acceptable salts and solvates thereof, and combinations of any two or more of the foregoing.

22. The method as defined in claim 18 wherein the drug comprises a substance selected from the group consisting of beclomethasone dipropionate, butixocort propionate, pirbuterol, 4-amino-$\alpha,\alpha$,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and combinations of any two or more of the foregoing.

23. The method as defined in claim 18 wherein the drug is in solution.

24. The method as defined in claim 18 wherein the drug is in suspension.

25. The method as defined in claim 24 wherein the drug comprises particles having a diameter of less than about 10 micrometers.

26. The method as defined in claim 18 wherein the medicinal composition is in a form that can be administered as an aerosol.

27. A method for the manufacture of a medicinal composition comprising:
   (a) Providing a biocompatible polymer comprising oligolactic acid;
   (b) Acetylating the biocompatible polymer to provide acetyl oligolactic acid and a mixed anhydride of acetyl oligolactic acid and acetic acid;
   (c) Reacting the mixed anhydride with a tertiary alcohol to provide an ester that can be chemically converted to an acid comprising acetyl oligolactic acid in the absence of water;
   (d) Converting the ester to acetyl oligolactic acid; and
   (e) Combining the acetyl oligolactic acid with a drug to provide the medicinal composition.

28. The method as defined in claim 27 wherein reacting the mixed anhydride with a tertiary alcohol comprises reacting the mixed anhydride with an alcohol selected from the group consisting of benzyl alcohol, t-butanol, derivatives of benzyl alcohol, derivatives of t-butanol and combinations of two or more of the foregoing.

29. The method as defined in claim 27 wherein the drug comprises a substance selected from the group consisting of antiallergics, analgesics, bronchodilators, antihistamines, antiviral agents, antitussives, anginal preparations, antibiotics, antiinflammatories, immunomodulators, 5-lipoxygenase inhibitors, leukotriene antagonists, phospholipase A 2 inhibitors, phosphodiesterase IV inhibitors, peptides, proteins, steroids, vaccine preparations and combinations of any two or more of the foregoing.

30. The method as defined in claim 27 wherein the drug comprises a substance selected from the group consisting of adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentamidine isoethionate, pirbuterol, prednisolone, salmeterol, terbutaline, tetracycline, 4-amino-$\alpha,\alpha$,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea and pharmaceutically acceptable salts and solvates thereof, and combinations of any two or more of the foregoing.

31. Method as defined in claim 27 wherein the drug comprises a substance selected from the group consisting of beclomethasone dipropionate, butixocort propionate, pirbuterol, 4-amino-$\alpha,\alpha$,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and combinations of any two or more of the foregoing.

32. The method as defined in claim 27 wherein the drug is in solution.

33. The method as defined in claim 27 wherein the drug is in suspension.

34. The method as defined in claim 33 wherein the drug comprises particles having a diameter of less than about 10 micrometers.

35. The method as defined in claim 27 wherein the medicinal composition is in a form that can be administered as an aerosol.

* * * * *

UNITED STATES PATENT AND TRADEMARK OFFICE
CERTIFICATE OF CORRECTION

| | | |
|---|---|---|
| PATENT NO. | : 7,597,897 B2 | Page 1 of 1 |
| APPLICATION NO. | : 10/596836 | |
| DATED | : October 6, 2009 | |
| INVENTOR(S) | : John T Capecchi | |

It is certified that error appears in the above-identified patent and that said Letters Patent is hereby corrected as shown below:

<u>Title Page 1, Abstract</u>
Column 2, line 11, Delete "water," and insert -- water; --, therefor.

<u>Title Page 2, Other Publications</u>
Line 10, delete ""New.biodegradable" and insert -- "New biodegradable --, therefor.

<u>Column 7</u>
Line 26, delete "—OCH" and insert -- —(OCH --, therefor.

Signed and Sealed this
Twenty-fourth Day of May, 2011

David J. Kappos
*Director of the United States Patent and Trademark Office*